United States Patent [19]

Segura

[11] Patent Number: 5,554,306

[45] Date of Patent: Sep. 10, 1996

[54] SULFITED FATTY COMPOUNDS WITH A REDUCED CONTENT OF FREE HYDROGEN SULFITE

[75] Inventor: Ramon Segura, Barcelona, Spain

[73] Assignee: Henkel Kommanditgesellschaft auf Aktien, Duesseldorf, Germany

[21] Appl. No.: 446,771

[22] PCT Filed: Nov. 22, 1993

[86] PCT No.: PCT/EP93/03274

§ 371 Date: May 30, 1995

§ 102(e) Date: May 30, 1995

[87] PCT Pub. No.: WO94/12471

PCT Pub. Date: Jun. 9, 1994

[30] Foreign Application Priority Data

Nov. 30, 1992 [DE] Germany .................. 42 40 159.3

[51] Int. Cl.$^6$ .................. C14C 9/00; C14C 11/00
[52] U.S. Cl. .................. 252/8.57; 8/94.22; 8/94.23; 554/88
[58] Field of Search .................. 252/8.57; 554/88; 8/94.23, 94.22

[56] References Cited

U.S. PATENT DOCUMENTS

| Re. 34,986 | 7/1995 | Rathfelder et al. | 8/94.33 |
|---|---|---|---|
| 4,741,738 | 5/1988 | Friese et al. | 8/94.23 |
| 4,744,794 | 5/1988 | Friese et al. | 8/94.23 |
| 4,755,187 | 7/1988 | Friese et al. | 8/94.23 |
| 4,800,045 | 1/1989 | Friese et al. | 554/88 |
| 4,897,225 | 1/1990 | Brehn et al. | 8/94.22 |
| 4,903,362 | 2/1990 | Friese et al. | 8/94.23 |
| 5,011,499 | 4/1991 | Rathfelder et al. | 8/94.33 |

FOREIGN PATENT DOCUMENTS

| 0247490 | 12/1987 | European Pat. Off. . |
|---|---|---|
| 0247509 | 12/1987 | European Pat. Off. . |
| 3317422 | 11/1986 | Germany . |

OTHER PUBLICATIONS

J. Int. Soc. Leath. Trad. Chem. 379 (1952) No Month.
Ledertechn. Rundsch. 1, (1949) No Month.
Przegl. Skorzany 42(2), 35 (cf. Chem. Abstracts 107(18):156865z) No Date.
Leder 8, 5 (1957) No Month.
Leder, Schuh, Lederwaren 21, 282 (1986) No Month.
Roempp, Chemie-lexikon, Thieme Verlag, Stuttgart, 9th Edition, vol. 11, p. 1498 (1990) No Month.

Primary Examiner—Anthony Green
Attorney, Agent, or Firm—Ernest G. Szoke; Wayne C. Jaeschke; Real J. Grandmaison

[57] ABSTRACT

Sulfited fatty compounds having a reduced content of free hydrogen sulfite are prepared by blowing unsaturated fatty compounds in an oxygen atmosphere at 100° C. to 150° C., sulfiting the blown fatty compounds with sodium metabisulfite, and subsequently fixing unreacted hydrogen sulfite as sulfosuccinic acid ester by aftertreatment with maleic acid esters, and optionally, a basic material.

21 Claims, No Drawings ns with a
SULFITED FATTY COMPOUNDS WITH A REDUCED CONTENT OF FREE HYDROGEN SULFITE

BACKGROUND OF THE INVENTION

1. Field of the Invention

This invention relates to sulfited fatty compounds with a reduced content of free hydrogen sulfite, to a process for their production, in which unsaturated fatty compounds are blown and sulfited and unreacted hydrogen sulfite is fixed as sulfosuccinates by aftertreatment with maleic acid esters and optionally bases, and to the use of the sulfited fatty compounds as leather auxiliaries.

2. Discussion of Related Art

Apart from tanning agents, oiling agents are the most important auxiliaries for bringing out the character of leather. Oiling agents develop their effect by fiber-insulating lubrication and by hydrophobicization.

The coating of the leather fibers with a fatty film reduces mutual friction and, hence, improves the suppleness and elasticity of the tissue. This has positive effects on the tear strength of the leather because, in an elastic material, many fibers—when subjected to tensile stressing—align themselves in the same direction as the tensile stress and then offer greater resistance to tearing than the same fibers in a brittle material. In addition, tanning effects are obtained through the hydrophobicization because hydrophobicization is accompanied by the displacement of water from the skin.

Vegetable and animal oils, fats and waxes and the hydrolysis, sulfonation, oxidation and hydrogenation products obtained therefrom by chemical conversion and, finally, mineral oiling agents are generally used for oiling leather. More specifically:

Saponifiable fats and oils and natural waxes and resins belong to the esters. Oils and fats are understood by the leather expert to be esters of glycerol and fatty acids which are solid or liquid at room temperature. From the group of animal fats, train oils, fish oil, beef tallow and neat's foot oil in particular and, from the group of vegetable fats, castor oil, rapeseed oil and linseed oil are used for oiling leather. In waxes and resins, the fatty acids are esterified with relatively high molecular weight alcohols instead of glycerol. Examples of waxes are beeswax, chinese wax, carnauba wax, montan wax and wool grease. The most important resins include colophony, birch bark oil and shellac.

The chemical conversion of vegetable and animal fats gives products which are soluble in water and which, in addition, emulsify water-insoluble fatty compounds to different extents. Known products include, for example, the sulfonated water-soluble oils of various kinds, train oils modified by oxidation which are known as degras or moellon, the soaps formed in the hydrolysis of natural fats, hydrogenated fats and, finally, free fatty acids, such as stearic acid, as baking fats. Most animal and vegetable fats have a certain affinity for leather which is considerably enhanced by the introduction or exposure of hydrophilic groups.

Mineral oiling agents are also important in leather manufacture. These hydrocarbons are similar to natural fats and oils in certain properties, but cannot be saponified. They are fractions from the distillation of petroleum which are known as mineral oil in liquid form, as vaseline in paste-like form and as paraffin in solid form.

In many cases, however, unwanted stains known as fatty spew are formed over a period of time on the surface of tanned and oiled leather. Fatty spew is mainly formed on chrome-tanned leather after relatively short or prolonged storage as a white, often bloom-like coating which only covers individual parts of the leather surface or even the entire leather surface. Fatty spew is attributable to the secretion of solid fatty compounds from the leather. It can be caused by the natural fat present in the leather or by fatty compounds which have been incorporated in the leather during the oiling process.

Fatty mixtures used to oil leather tend to form fatty spew in particular when they contain many free fatty acids. Free fatty acids generally have a higher melting point than their glycerides. The hydrolysis of fatty compounds during storage of the leather increases the risk of fatty spew accordingly.

Soaps and fat liquors are hydrolyzed in chrome leather, especially in inadequately deacidified chrome leather, with release of fatty acids. Sulfonated oils and fats differ in their tendency to form fatty spew, the tendency to form fatty spew generally diminishing with the age of the leather [cf. J. Int. Soc. Leath. Trad. Chem. 379 (1952)].

Fatty spew is formed more easily, the greater the content of fatty compounds tending to form fatty spew in the leather. The quantity, composition and position of the fatty mixture of natural fat and fat liquor present in the leather are critical to the extent and composition of the fatty spew. Loosely structured leather tends to form fatty spew less than leather with a dense fiber structure. Fatty spew is observed more often at low temperatures than at relatively warm outside temperatures.

The crystalline fatty spew forms in the follicles and glandular channels, small crystals initially being formed deep inside the follicle and gradually filling the entire follicle as relatively large fatty crystals which then spread out over the surface of the leather and coalesce into a dense crystal film. Any fats containing stearin or palmitin derivatives can cause crystalline fatty spew, the danger of fatty spew increasing with increasing concentration [Ledertechn. Rundsch. 1 (1949)].

So-called neutral fats in particular, i.e. substances with no ionic groups in the molecule which are suitable for oiling leather, for example fats, waxes and hydrocarbons, tend to form fatty spew. Those neutral fats which are stearin and/or palmitin derivatives, such as for example corresponding triglycerides or the free fatty acids, are particularly critical in this regard.

Since oiling is virtually a compulsory step in the processing of leather, but after tanning, to establish the required product properties, it has become standard practice to use special synthetic oiling compositions with only a minimal tendency to form fatty spew.

One class of oiling agents widely used for this purpose are halogenated compounds, such as chlorinated hydrocarbons. Unfortunately, the increasing ecological and toxicological requirements which compositions entering the environment or coming into contact with the consumer are expected to satisfy make this class of compounds increasingly unattractive. The use of chloroparaffins as additives to fat liquor emulsions to prevent the formation of fatty spew on chrome-tanned pigskin is described, for example, by J. Golonka in Przegl. Skorzany 42(2), 35 (cf. Chem. Abstracts 107(18):156865z).

EP-B 0 247 509 (Stockhausen) describes adducts of sulfuric acid or oleum with unsaturated, alkoxylated and optionally epoxidized fats and oils. Unfortunately, products of this type generally have an unfavorably high electrolyte content so that the salts are in danger of crystallizing out and impairing the quality of the treated leather.

In addition to reactions with oleum, sulfuric acid or gaseous sulfur trioxide, sulfiting i.e. the addition of hydrogen sulfite onto unsaturated compounds, is particularly suitable for the hydrophilicization of fatty compounds. For example, A. Küntzel reports in this connection on the sulfiting of cod liver oil [Leder 8, 5 (1957)] while M. Mikula reports on the sulfiting of unsaturated fatty acid butyl esters [Leder, Schuh, Lederwaren 21, 282 (1986)]. Although sulfited fatty compounds show particularly favorable oiling behavior, they also tend to form unwanted fatty spew. Another disadvantage is that the products have a pungent odor attributable to small amounts of unreacted hydrogen sulfite.

Accordingly, the methods from the prior art for preventing fatty spew are not altogether satisfactory.

It is clear from the above context that there is a constant need in the leather industry for additives or oiling compositions which effectively prevent fatty spew so that the range of commercial products can be extended to allow a flexible response to the changing requirements of the market. More particularly, there is a need for ecologically or rather toxicologically safe additives and oiling compositions of which the use does not result in the unwanted formation of fatty spew.

Accordingly, the problem addressed by the present invention was to provide new substances for oiling and hydrophobicizing leather which would be free from the disadvantages mentioned above.

DESCRIPTION OF THE INVENTION

The present invention relates to sulfited fatty compounds with a reduced content of free hydrogen sulfite which are obtained by blowing unsaturated fatty compounds in known manner, sulfiting the blown fatty compounds with sodium metabisulfite and then fixing unreacted hydrogen sulfite as sulfosuccinic acid esters by aftertreatment with maleic acid esters and optionally bases.

It has surprisingly been found that the residual content of free hydrogen sulfite in blown sulfited fatty compounds can be significantly reduced to levels below 1% by weight, based on the solids content of the products, if the crude products are aftertreated with maleic acid esters and optionally bases. The invention is based on the observation that the free hydrogen sulfite reacts off quickly and almost completely with the maleic acid esters to form sulfosuccinic acid esters ("sulfosuccinates"). The sulfited fatty compounds according to the invention which contain sulfosuccinates show distinctly improved performance properties in relation to typical known products. More particularly, their tendency to form fatty spew on leather surfaces is significantly reduced, in addition to which the products are substantially odorless.

The present invention also relates to a process for the production of sulfited fatty compounds with a reduced content of free hydrogen sulfite, in which unsaturated fatty compounds are blown in known manner and sulfited with sodium hydrogen sulfite, after which unreacted hydrogen sulfite is fixed as sulfosuccinic acid esters by aftertreatment with maleic acid esters and optionally bases.

Starting Materials

Fatty acid glycerides, fatty acid lower alkyl esters or mixtures thereof may be used as the fatty compounds serving as starting materials for the production of the sulfited products.

a) Fatty acid glycerides are substances corresponding to formula (I):

in which —COR$^1$, COR$^2$ and COR$^3$ and R$^3$CO independently of one another represent aliphatic acyl radicals containing 12 to 24 carbon atoms and 1, 2, 3 or 4 double bonds.

The fatty acid glycerides may be of synthetic origin or, more particularly vegetable or animal origin. Typical examples are triglycerides which solely or predominantly contain palmitoleic acid, oleic acid, elaidic acid, petroselic acid, linoleic acid, linolenic acid, gadoleic acid, erucic acid, arachidonic acid and/or clupanodonic acid as fatty acid components. Preferred starting materials in this regard are glycerol trioleate and also vegetable or animal fats and oils which have an iodine value of 50 to 150 and preferably 80 to 140. Without any claim to completeness, olive oil, olive kernel oil, sunflower oil from old and new plants, rapeseed oil from old and new plants, cottonseed oil, peanut oil, coriander oil, linseed oil, beef tallow and fish oil are mentioned as examples of suitable vegetable and animal fats and oils. Commensurate with their nature, the vegetable and animal fats and oils may also have saturated components providing they do not exceed 50% by weight.

b) Fatty acid lower alkyl esters are substances corresponding to formula (II):

in which R$^4$CO represents aliphatic acyl radicals containing 12 to 24 carbon atoms and 1, 2, 3 or 4 double bonds and R$^5$ represents linear or branched alkyl radicals containing 1 to 4 carbon atoms.

Typical examples are ethyl, propyl, butyl and, more particularly, methyl esters of palmitoleic acid, oleic acid, elaidic acid, petroselic acid, linoleic acid, linolenic acid, gadoleic acid, erucic acid, arachidonic acid and/or clupanodonic acid and the technical mixtures thereof obtained, for example, in the pressure hydrolysis of the vegetable and animal fats and oils mentioned above. Oleic acid and/or linoleic acid methyl ester is/are preferably used.

As mentioned above, the fatty acid glycerides and the fatty acid lower alkyl esters may be used both individually and in the form of mixtures. However, it has proved to be of particular advantage to sulfite mixtures of unsaturated fatty acid glycerides and unsaturated fatty acid lower alkyl esters together. The molar mixing ratio may vary over wide ranges and may be, for example, 1:5 to 5:1 and preferably 1:1 to 3:1.

Blowing and Sulfiting

The blowing of fatty compounds is a known process in which (atmospheric) oxygen is introduced into unsaturated fatty compounds at 100° to 150° C. The object of blowing is to increase the viscosity and stability of the fatty compounds by partial autoxidation [cf. ROEMPP, Chemielexikon, Thieme Verlag, Stuttgart, 9th Edition, Vol. II, page 1498 (1990)]. In the context of the process according to the invention, it has proved to be of advantage to blow fatty acid compounds at 100° to 110° C. until an increase in density of around 0.01 to 0.1 g/cm$^3$ and preferably 0.02 to 0.5 g/cm$^3$ is reached.

Sulfiting can be carried out in known manner, sodium hydrogen sulfite being added onto the double bond of the unsaturated fatty compounds. Since sodium hydrogen sulfite is only stable in aqueous solution, sodium metabisulfite ($Na_2SO_3$) is used as the sulfiting agent. The unsaturated fatty compounds and the sodium metabisulfite may normally be used in a molar ratio of 3:1 to 15:1 and preferably 5:1 to 10:1, based on the double bond equivalents in the unsaturated fatty compounds. It has proved to be optimal to carry out the sulfiting step over a period of 1 to 5 h and preferably 2 to 4 h at temperatures of 50° to 120° C. and preferably 60° to 90° C.

Aftertreatment

According to the invention, hydrogen sulfite unreacted in the sulfiting step is fixed as sulfosuccinic acid ester ("sulfosuccinate") by aftertreatment with a maleic acid ester.

Suitable maleic acid esters are compounds corresponding to formula (IV):

$$R^7COO—CH=CH—COOR^{89} \quad (IV)$$

in which $R^7$ is an alkyl and/or alkenyl radical containing 6 to 22 carbon atoms and $R^8$ is hydrogen or an alkyl and/or alkenyl radical containing 6 to 22 carbon atoms. Typical examples are monoesters or diesters of maleic acid or maleic anhydride with caproic alcohol, caprylic alcohol, capric alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachinyl alcohol, gadoleyl alcohol, behenyl alcohol and erucyl alcohol and the technical mixtures thereof obtained, for example, in the hydrogenation of technical methyl ester fractions or aldehydes from Roelen's oxo synthesis. Maleic acid monoesters of technical cocofatty alcohols or tallow fatty alcohols, more particularly oleyl alcohol, are preferably used.

The maleic acid esters may be used in quantities of 10 to 100 mole-%, based on the quantity of sodium metabisulfite used. The quantity used will normally be selected to correspond to the residual content of free hydrogen sulfite. Accordingly, a quantity of 15 to 30 mole-%, again based on the quantity of metabisulfite used, is the preferred choice. However, with the performance properties of the product in mind, it may be that the concentration of sulfosuccinate achieved by reaction of the free hydrogen sulfite with the maleic acid ester is not sufficient. In this case, the percentage of free metabisulfite in the crude sulfiting product can be artificially increased, for example from 15% to 35% by weight, based on the solids content of the product. The expert will be able to take this aspect into account as a matter of course when selecting the quantity of maleic acid ester without having to become involved in any inventive activity.

The aftertreatment of the crude sulfiting products with the maleic acid esters may be carried out in the presence of aqueous bases, such as for example alkali metal or alkaline earth metal hydroxides or ammonia. Since it is the function of the base to neutralize free carboxyl groups of the maleic acid or sulfosuccinic acid ester (where present), its quantity will intentionally be selected so that a pH value at which there is no danger of saponification of the ester bonds is established in the product.

The aftertreatment may be carried out over a period of 0.5 to 5 h and preferably 1 to 3 h at temperatures of 50° to 90° C. and preferably 70° to 85° C.

Industrial Applications

The sulfited fatty compounds provide leather with a pleasant suppleness and with resistance to moisture. They are substantially odorless, have no tendency to form fatty spew and are readily biodegradable. Since free hydrogen sulfite does not adhere to the leather, but instead is washed out after the oiling treatment, the comparatively low electrolyte content of the sulfited fatty compounds according to the invention is an additional advantage from the ecological point of view.

Accordingly, the present invention also relates to leather oiling compositions, more particularly for chrome-tanned leather, which may contain from 1% to 99% by weight and preferably from 10% to 50% by weight of the sulfited fatty compounds according to the invention. In addition to the fatty compounds according to the invention, these oiling compositions may contain other typical additives, such as for example fatty acid esters and dialkyl ethers.

Finally, the present invention relates to the use of the sulfited fatty compounds according to the invention for the production of oiling and hydrophobicizing compositions, more particularly for chrome-tanned leather, in which they may be present in quantities of 1% to 99% by weight and preferably 10% to 50% by weight.

The following Examples are intended to illustrate the invention without limiting it in any way.

EXAMPLES

Example 1

A mixture of 250 g (0.2 mole) of fish oil (saponification value 130, iodine value 145) and 500 g (0.55 mole) of olive kernel oil (saponification value 185, iodine value 95) was introduced into a 2-liter three-necked flask equipped with a stirrer, reflux condenser and dropping funnel and blown with air at 105° C. until an increase in density of 0.03 g/cm³ (as measured at 20° C.) was obtained. The mixture was then cooled to 60° C. and a solution of 90 g (0.9 mole) of sodium metabisulfite in 170 ml of deionized water was added in portions through the dropping funnel. After the addition, the reaction mixture was heated to 85° C. and stirred for another 2 h at that temperature. Unreacted hydrogen sulfite was then fixed as sulfosuccinic acid monoester by the addition of 75 g (0.2 mole) of maleic acid monooleyl ester and 20 g (0.85 mole) of ammonia in the form of a 50% by weight aqueous solution. The residual content of free hydrogen sulfite was 0.5% by weight, based on the solids content of the sulfited product.

Example 2

A mixture of 250 g (0.2 mole) of fish oil, 250 g (0.28 mole) of glycerol trioleate and 250 g (0.84 mole) of olive kernel oil fatty acid methyl ester was blown at 105° C. as in Example 1 until an increase in density of 0.03 g/cm³ was obtained and was then sulfited with 68 g (0.68 mole) of sodium metabisulfite in 120 ml of water. Unreacted hydrogen sulfite and another 22 g (0.22 mole) of sodium metabisulfite, which had been added to the fully reacted reaction mixture, were then fixed as sulfosuccinic acid monoester by addition of 75 g (0.2 mole) of maleic acid monooleyl ester and 20 g (0.85 mole) of ammonia in the form of a 25% by weight aqueous solution. The residual content of free hydrogen sulfite was 0.9% by weight, based on the solids content of the sulfited product.

I claim:

1. Sulfited fatty compounds having a reduced content of free hydrogen sulfite prepared by blowing unsaturated fatty compounds in an oxygen atmosphere at 100° C. to 180° C., sulfiting the blown fatty compounds with sodium metabisulfite, and subsequently fixing unreacted hydrogen sulfite as sulfosuccinic acid ester by aftertreatment with maleic acid esters, and optionally, a basic material.

2. The process of producing sulfited fatty compounds having a reduced content of free hydrogen sulfite, comprising blowing unsaturated fatty compounds in an oxygen atmosphere at 100° C. to 150° C., sulfiting the blown fatty compound with sodium metabisulfite, and fixing unreacted hydrogen sulfite as sulfosuccinic acid ester by aftertreatment with maleic acid esters, and optionally, a basic material.

3. A process as in claim 2 wherein said unsaturated fatty compounds are selected from the group consisting of fatty acid glycerides, fatty acid lower alkyl esters, and mixtures thereof.

4. A process as in claim 3 wherein said fatty acid glycerides correspond to formula (I):

in which $COR^1$, $COR^2$ and $COR^3$ independently of one another represent aliphatic acyl radicals containing 12 to 24 carbon atoms and 1, 2, 3 or 4 double bonds.

5. A process as in claim 3 wherein said fatty acid lower alkyl esters correspond to formula (II):

$$R^4CO-OR^5 \qquad (II)$$

in which $R^4CO$ represents alipatic acyl radicals containing 12 to 24 carbon atoms and 1, 2, 3 or 4 double bonds, and $R^5$ represents linear or branched alkyl radicals containing 1 to 4 carbon atoms.

6. A process as in claim 2 wherein said unsaturated fatty compounds are blown in said oxygen atmosphere until an increase in density of 0.01 to 0.1 g/cm$^3$ is obtained.

7. A process as in claim 2 wherein said unsaturated fatty compounds and said sodium metabisulfite are present in a molar ratio of 3:1 to 15:1, based on double bond equivalents in said unsaturated fatty compounds.

8. A process as in claim 2 wherein said maleic acid esters correspond to formula (IV):

$$R^7COO-CH=CH-COOR^8 \qquad (IV)$$

in which $R^7$ is an alkyl or alkenyl radical containing 6 to 22 carbon atoms and $R^8$ is hydrogen or an alkyl or alkenyl radical containing 6 to 22 carbon atoms.

9. A process as in claim 2 wherein from 10 to 100 mole-%, based on the quantity of sodium metabisulfite used to sulfite said blown fatty compounds of said maleic acid esters is present to fix said untoacted hydrogen sulfite as sulfosuccinic acid ester.

10. A process as in claim 2 wherein said basic material is selected from the group consisting of alkali metal and alkaline earth metal hydroxides, and ammonia in the form of aqueous solutions.

11. A process as in claim 2 wherein said aftertreatment is carried out at a temperature of 50° C. to 90° C.

12. A leather treating composition containing sulfited fatty compounds having a reduced content of free hydrogen sulfite prepared by blowing unsaturated fatty compounds in an oxygen atmosphere at 100° C. to 150° C., sulfiting the blown fatty compounds with sodium metabisulfite, and subsequently fixing unreacted hydrogen sulfite as sulfosuccinic acid ester by aftertreatment with maleic acid esters, and optionally, a basic material.

13. A leather treating composition as in claim 12 wherein said unsaturated fatty compounds are selected from the group consisting of fatty acid glycerides, fatty acid lower alkyl esters, and mixtures thereof.

14. A leather treating composition as in claim 13 wherein said fatty acid glycerides correspond to formula (I):

in which $COR^1$, $COR^2$ and $COR^3$ independently of one another represent aliphatic acyl radicals containing 12 to 24 carbon atoms and 1, 2, 3 or 4 double bonds.

15. A leather treating composition as in claim 13 wherein said fatty acid lower alkyl esters correspond to formula (II):

$$R^4CO-OR^5 \qquad (II)$$

in which $R^4CO$ represents aliphatic acyl radicals containing 12 to 24 carbon atoms and 1, 2, 3 or 4 double bonds, and $R^5$ represents linear or branched alkyl radicals containing 1 to 4 carbon atoms.

16. A leather treating composition as in claim 12 wherein said unsaturated fatty compounds are blown in said oxygen atmosphere until an increase in density of 0.01 to 0.1 g/cm$^3$ is obtained.

17. A leather treating composition as in claim 12 wherein said blown fatty compounds and said sodium metabisulfite have been reacted in a molar ratio of 3:1 to 15:1, based on double bond equivalents in said fatty compounds.

18. A leather treating composition as in claim 12 wherein said maleic acid esters correspond to formula (IV):

$$R^7COO-CH=CH-COOR^8 \qquad (IV)$$

in which $R^7$ is an alkyl or alkenyl radical containing 6 to 22 carbon atoms and $R^8$ is hydrogen or an alkyl or alkenyl radical containing 6 to 22 carbon atoms.

19. A leather treating composition as in claim 12 wherein from 10 to 100 mole-%, based on the quantity of sodium metabisulfite used to sulfite said blown fatty compounds, of said maleic acid esters is present to fix said unreacted hydrogen sulfite as sulfosuccinic acid ester.

20. A leather treating composition as in claim 12 wherein said basic material is selected from the group consisting of alkali metal and alkaline earth metal hydroxides, and ammonia in the form of aqueous solutions.

21. A leather treating composition as in claim 12 wherein said aftertreatment is carried out at a temperature of 50° C. to 90° C.

* * * * *